(12) United States Patent
Anderson et al.

(10) Patent No.: US 6,569,670 B2
(45) Date of Patent: May 27, 2003

(54) FERMENTATION PROCESS

(75) Inventors: Kevin W. Anderson, Indian Springs, OH (US); J. Douglas Wenzel, Cincinnati, OH (US)

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 09/754,158

(22) Filed: Jan. 4, 2001

(65) Prior Publication Data

US 2002/0028499 A1 Mar. 7, 2002

Related U.S. Application Data

(63) Continuation-in-part of application No. 09/663,963, filed on Sep. 19, 2000.
(60) Provisional application No. 60/175,174, filed on Jan. 7, 2000, and provisional application No. 60/156,791, filed on Sep. 30, 1999.

(51) Int. Cl.$^7$ .............................. C12N 1/20; C12P 7/00; C12P 7/40
(52) U.S. Cl. ...................... 435/253.6; 435/132; 435/136
(58) Field of Search ................................. 435/132, 136, 435/253.6

(56) References Cited

U.S. PATENT DOCUMENTS

| 4,919,836 A | | 4/1990 | Meijer et al. |
|---|---|---|---|
| 5,733,774 A | * | 3/1998 | Jin et al. |
| 5,962,285 A | | 10/1999 | Anderson et al. |
| 6,004,784 A | | 12/1999 | Mobley et al. |

OTHER PUBLICATIONS

Difco Manual, . 1985, Difco Laboratories, Detroit, MI. p. 1136.*
International Search Report for International Appln. No. PCT/US01/00471.

* cited by examiner

Primary Examiner—Christopher R. Tate
Assistant Examiner—Kaiash C. Srivastava
(74) Attorney, Agent, or Firm—John E. Drach

(57) ABSTRACT

A fermentation medium containing: (a) a source of metabolizable carbon and energy; (b) a source of inorganic nitrogen; (c) a source of phosphate; (d) at least one metal selected from the group consisting of an alkali metal, an alkaline earth metal, a transition metal, and mixtures thereof; and (e) biotin, substantially free of particulate matter and bacteria. A fatty material may be added to an aqueous suspension containing at least one dicarboxylic acid to modify the rheological characteristics of the suspension.

14 Claims, 1 Drawing Sheet

FERMENTATION PROCESS

CROSS-REFERENCE TO RELATED APPLICATIONS

This application is a continuation-in-part of copending U.S. application Ser. No. 09/663,963, filed Sep. 19, 2000 and claims the benefit of previously copending provisional application Ser. No. 60/156,791 filed on Sep. 30, 1999, and copending provisional application Ser. No. 60/175,174 filed on Jan. 7, 2000.

STATEMENT REGARDING FEDERALLY SPONSORED RESEARCH OR DEVELOPMENT

This invention was funded, at least in part, under a grant from the Department of Commerce, NIST-ATP Cooperative Agreement Number 70NANB8H4033. The Government may therefore have certain rights in the invention.

BACKGROUND OF THE INVENTION

This invention relates to an improved fermentation medium and process for making an aliphatic polycarboxylic acid using said medium.

Long-chain alpha, omega-dicarboxylic acids, i.e., those having a carbon number of 9 or higher, are used as raw materials in the synthesis of a variety of chemical products and polymers.

Diacids with carbon numbers greater than four are currently produced almost exclusively by nonbiological conversion processes. These types of chemical processes for the production of diacids have a number of limitations and disadvantages. Each process is restricted to the production of diacids of specific carbon chain lengths, based on the starting material used. For example, the dodecandioic acid process begins with butadiene, therefore the products of this reaction process are limited to acids with chain lengths in multiples of four. In addition, the processes are based on nonrenewable petrochemical feedstocks, and the multireaction conversion process produces unwanted byproducts which result in yield losses, heavy metal wastes, and nitrogen oxides which must be destroyed in a reduction furnace.

Biological conversion processes for the production of diacids have a number of potential advantages relative to the existing non-biological conversion processes. Primary among these is the use of renewable feedstocks as starting materials and the ability to produce the diacid without the generation of hazardous chemical byproducts which necessitate costly waste disposal processes.

Another important advantage achieved by using a biological process is that such a process can easily be adapted to produce a wide variety of diacids using the same biocatalyst and the same equipment. Because current organic chemical syntheses are suited to the production of only a single diacid, the synthesis of several different diacids would require the development of a new synthetic scheme for each diacid. On the other hand, a yeast biocatalyst can be used to produce diacids of varying lengths using the same equipment, media and protocols merely by providing a different substrate to the yeast.

U.S. Pat. No. 6,004,784, the entire contents of which is hereby incorporated by reference, discloses a semi-synthetic fermentation medium which employs corn steep liquor and brewers yeast extract in order to reduce the cost of conventional fermentation media which contain expensive, highly standardized yeast extracts and yeast nitrogen bases.

The problem associated with the use of such inexpensive substitutes is many fold. They result in a fermentation broth having significant odor emissions when sparged with air. Particulate matter, especially combined with high levels of bacteria, contained in corn steep liquor and crude yeast extracts make them difficult to sterilize and contribute to the bioburden on media sterilization equipment. These substitutes also contain many unmetabolizable components that contribute to color and color stability problems which need to be attended to using additional purification steps with their incumbent product losses. The selection of these substitutes, while lowering media cost, add additional process costs. Consequently, there remains a need for a low-cost, biofermentation medium which provides nutrients to support growth of the yeast biocatalysts permitting high specific productivity of polycarboxylic acids, polyols, and polyhydroxy acids.

Although long chain dicarboxylic acids have limited solubility in water in their undissociated or partial salt form, there are many cases where it is necessary to handle them in an aqueous medium. Examples include fermentation and recovery processes used to produce dicarboxylic acids, interfacial polymerization reactions, emulsion polymerization reactions, and enzymatic reactions.

Aqueous suspensions of long chain dicarboxylic acids tend to be highly viscous and are therefore difficult to handle. Major operational issues in fermentation reactions used to prepare dicarboxylic acids include oxygen transfer, heat transfer, gas hold-up in the fermentation broth, and broth hold-up in the exiting gas (foaming) each being affected by the Theological characteristics of the broth. Likewise, in filtration processes used to recover dicarboxylic acids from the fermentation broth, high viscosity leads to impractical filtration rates. In polymerization and enzyme reactions, viscosity effects on mass transfer would be a major issue since it is desirable to have rapid, predictable contact of reagents.

In DE 29 09 420 A1, Watanabe, et al. describes a method for treating suspensions of long-chain dicarboxylic acids in cell-free fermentation broth to improve filtration rates and purity of recovered diacids. He demonstrated that by heating the aqueous dicarboxylic acid suspension at pH 4 or below to above 50° C. for 1 hour or more, he could control the particle size distribution and particle morphology. He describes that by growing the particles to an average particle size of 40–50 $\mu$m he could obtain improved filtration rates, lower filter cake moisture, and higher dicarboxylic acid purity in the filter cake. Unfortunately, this method has limited utility for many applications where aqueous suspensions of long chain dicarboxylic acids are encountered.

Many fermentation and enzyme reactions occur over a broader pH range and below 50° C. In many cases, enzyme and microbial activity would be reduced or destroyed under the conditions described by Watanabe, et al. Interfacial and emulsion polymerization reactions involving aqueous dicarboxylic acid suspensions could only be limited to thermally stable reagents. There is therefore a need for alternative methods of controlling rheological properties of aqueous suspensions of long chain dicarboxylic acids.

SUMMARY OF THE INVENTION

In one aspect, the present invention is directed to a fermentation medium and process for making polycarboxylic acids, polyols, and polyhydroxy acids using said medium. The fermentation medium contains:

(a) a source of metabolizable carbon and energy;

(b) a source of inorganic nitrogen;

(c) a source of phosphate;

(d) at least one metal selected from the group consisting of alkali metals, alkaline earth metals, transition metals, and mixtures thereof; and (e) a source of biotin, substantially free of particulate matter and bacteria.

The present invention is also directed to a process for making polycarboxylic acids, polyols and polyhydroxy acids involving:

(a) providing an organism capable of producing a polycarboxylic acid, a polyol or a polyhydroxy acid;

(b) providing a substrate capable of being converted into a polycarboxylic acid, a polyol or a polyhydroxy acid by the organism;

(c) providing a fermentation medium containing:

(i) a source of metabolizable carbon and energy;

(ii) a source of inorganic nitrogen;

(iii) a source of phosphate;

(iv) at least one metal selected from the group consisting of alkali metals, alkaline earth metals, transition metals, and mixtures thereof; and (v) a source of biotin, substantially free of particulate matter and bacteria; and (d) fermenting the organism in the fermentation medium.

The present invention also relates to an aqueous suspension containing at least one dicarboxylic acid which also includes water, and a fatty material in an amount effective to cause formation of substantially disk shaped, substantially partially spherical shaped or substantially spherical shaped dicarboxylic acid particles.

The present invention also relates to a method for modifying the rheological properties of an aqueous suspension containing a dicarboxylic acid including adding an effective dicarboxylic acid particle shape forming amount of fatty material to the suspension to cause formation of shaped dicarboxylic acid particles, wherein the shape is selected from the group consisting of substantially disk shaped, substantially partially spherical shaped and substantially spherical shaped.

DESCRIPTION OF THE INVENTION

Figure 1:
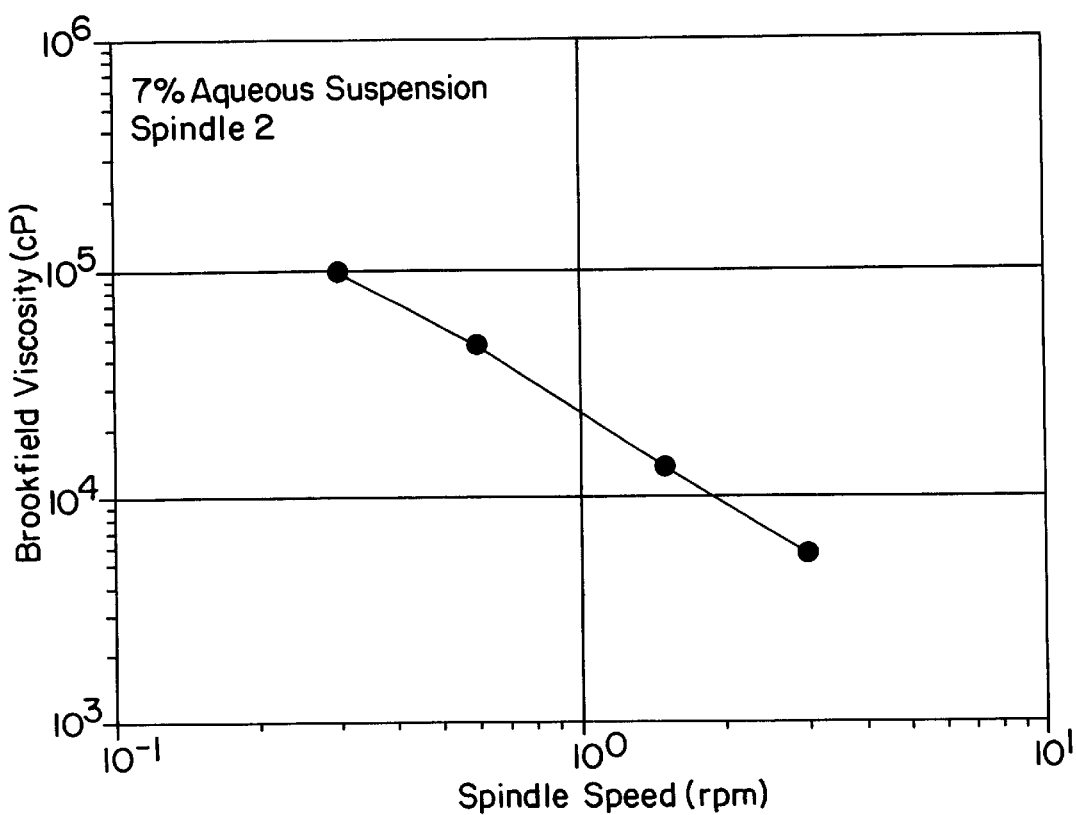
FIG. 1 is a graphic depiction of the Brookfield viscosity of a 7% aqueous fermentation broth suspension of dicarboxylic acids using a fatty material to modify the rheological properties of the broth.

All numbers expressing quantities of ingredients and/or reaction conditions are to be understood as being modified in all instances by the term "about".

Through the judicious selection of alternative nutrients that support microbial growth, the invention provides a medium which allows important polyfunctional materials to be produced commercially, in large quantity, using a biological conversion process. The invention provides a low cost alternative to prior art media and methods for its use that is easily prepared and sterilized, has a low degree of odor, provides a lower contribution of impurities loading in subsequent downstream processes, yet results in the production of product in at least as high a yield as conventional prior art methods. It is surprising that the myriad of undefined components comprising corn steep liquor and yeast extract can be replaced by relatively few components without sacrificing the quality of microbial growth and productivity of polyfunctional compounds.

Thus, according to one aspect of the present invention, there is provided an economical fermentation medium capable of facilitating the bioconversion of various types of organic substrates. The fermentation medium contains the following necessary components: (i) a source of metabolizable carbon and energy; (ii) a source of inorganic nitrogen; (iii) a source of phosphate; (iv) at least one metal selected from the group consisting of alkali metals, alkaline earth metals, and mixtures thereof, and (v) a source of biotin, substantially free of particulate matter and bacteria. These materials alone satisfy the basic nutritional requirements for growing the microorganism yet produce biomass of sufficient quantity and quality to conduct the bioconversion.

Suitable sources of metabolizable carbon and energy include but are not limited to glucose, fructose, maltose, glycerol, sodium acetate, methanol, short chain alcohols, and mixtures thereof. The preferred source of metabolizable carbon and energy is glucose, preferably a liquid glucose syrup, for example, 95% dextrose-equivalent syrup, or even lower dextrose-equivalent syrups. Such materials contain small amounts of disaccharides, trisaccharides, and polysaccharides which can be hydrolyzed during the fermentation by the addition of an amylase enzyme such as amylase, glucoamylase and cellulase. Thus, glucose can be provided in situ in a reaction simultaneous with the biooxidation.

Inorganic sources of nitrogen include but are not limited to alkali metal nitrates such as sodium or potassium nitrate, ammonium salts such as ammonium sulfate, ammonium chloride, ammonium nitrate and ammonium acetate. A preferred inorganic nitrogen source is ammonia or ammonium hydroxide.

Another necessary component of the fermentation medium of the present invention is a source of phosphate which includes any phosphate-containing compounds. Examples thereof include, but are not limited to, potassium phosphate, sodium phosphate, and ammonium phosphate. A particularly preferred source of phosphate for use in the present invention is potassium phosphate.

Suitable metals for use in the fermentation medium include alkali metals, alkaline earth metals, transition metals, and mixtures thereof. Particularly preferred metals include potassium, calcium, and magnesium, in combination.

The last critical component of the fermentation medium is biotin which is substantially free of particulate matter and bacteria.

Any of the medium components may be added as a part of the initial sterile media charge, sterilized as concentrated aqueous solutions for later addition to the fermentation medium, or may be included in large excess in the fermentor inoculum for carry-over into the production fermentor.

In order to avoid problems associated with odor emission, color instability, and contamination, it is imperative that the biotin be free of particulate matter and bacteria which promote such problems and require additional process purification steps. The quantity of biotin required will be several orders of magnitude smaller than the organic nitrogen sources it replaces in prior art media.

The fermentation medium of the present invention contains in aqueous solution: (a) from about 10 g/l to about 60 g/l, preferably from about 20 g/l to about 40 g/l of a source of metabolizable carbon and energy, preferably glucose; (b) from about 50 ppm to about 2000 ppm, preferably from about 50 ppm to about 250 ppm, and most preferably from about 100 ppm to about 250 ppm, of nitrogen provided by the inclusion of an inorganic nitrogen source; (c) from about 1 g/l to about 10 g/l, preferably from about 1 g/l to about 7 g/l, of a source of phosphate, preferably potassium phosphate; (d) from about 0.01 g/l to about 2 g/l, preferably from about 0.01 g/l to about 1 g/l of at least one metal selected from the group consisting of alkali metals, alkaline earth metals, and mixtures thereof, preferably a mixture of calcium and magnesium; and (e) from about 1 $\mu$g/l to about 2000 $\mu$g/l, preferably from about 4 $\mu$g/l to about 200 $\mu$g/l, and most preferably from about 4 $\mu$g/l to about 20 $\mu$g/l of biotin, wherein the biotin is substantially free of deleterious particulate matter and bacteria.

The water present in the fermentation medium may be a process water purified by distillation, deionization, or softening. Preferred sources of water include those from a municipal water distribution system, a process recycle stream, or well water wherein adjustments in mineral content may need to be taken into account for minerals already contained in these sources of water. For example, the water together with other required ingredients may already contain sufficient mineral components to provide all or substantially all the required minerals for growth of the organism.

The fermentation media of the present invention satisfies the basic nutrient requirements for the growth of the microorganism, while minimizing the addition of organic and inorganic components that require separation from the product for disposal as waste and contribute to process odor emissions. In contrast to fermentation media compositions known in the art, the media of the present invention contains no particulate matter, is particularly amenable to continuous sterilization in an automated medium preparation process, and is inexpensive. Despite the nutritionally lean media compositions provided by the present invention, there is broad flexibility in formulating the media while achieving high productivities of polycarboxylic acids, polyols, and polyhydroxy acids.

Various types of auxiliary components may also be employed in the fermentation medium of the present invention in order to further enhance the biofermentation process. Examples thereof include, but are not limited to, various types of trace metals, chelating agents, anti-foaming agents, and the like.

The fermentation media of the present invention may be used with any polycarboxylic acid-producing, polyol-producing and polyhydroxy acid-producing yeast, and a wide variety of substrates. For example, in the event that the desired product is a polycarboxylic acid, such as a diacid, any type of fatty acid, fatty acid ester, or alkane substrate may be used. Examples of suitable substrates for the production of diacids include, but are not limited to, lauric acid, myristic acid, palmitic acid, stearic acid, oleic acid, palmitoleic acid and methyl esters thereof, and mixtures thereof. Examples of alkanes include dodecane, dodecene, tridecane, tetradeance, octadecane, and the like.

Thus, according to another aspect of the present invention, there is provided a process for making a polycarboxylic acid, a polyol, or a polyhydroxy acid. For exemplary purposes only, the process of the present invention will be described with reference to making polycarboxylic acids, and specifically diacids, as the desired end product.

The process may be operated over any pH range where the microorganism can grow and catalyze the desired conversion reaction. A preferred and especially advantageous pH range is in the acidic regime, i.e., a pH of about 7 or less. While the low pH improvement can be applied to any fermentation process, it is especially advantageous when applied to a fermentation process which produces polycarboxylic acids. Suitable pH control reagents are ammonia, ammonium hydroxide solution, concentrated potassium or sodium hydroxide.

The organic substrate can be any organic compound that is biooxidizable to a mono- or polycarboxylic acid. Such a compound can be any saturated or unsaturated aliphatic compound or any carboxylic or heterocyclic aromatic compound having at least one terminal methyl group, a terminal carboxyl group and/or a terminal functional group which is oxidizable to a carboxyl group by biooxidation. A terminal functional group which is a derivative of a carboxyl group may be present in the substrate molecule and may be converted to a carboxyl group by a reaction other than biooxidation. For example, a lipase enzyme, for example, can be added during the fermentation step to liberate free fatty acids from an otherwise non-metabolizable ester.

Alkanes are a type of saturated organic substrate which are useful in practicing the process according to the invention. The alkanes can be linear or cyclic, branched or straight chain, substituted or unsubstituted. Particularly preferred alkanes are those having from about 4 to about 25 carbon atoms, examples of which include but are not limited to butane, hexane, octane, nonane, dodecane, tridecane, tetradecane, octadecane and the like.

Examples of unsaturated organic substrates which can be used in the process according to the invention include but are not limited to internal olefins such as 2-pentene, 2-hexene, 3-hexene, 9-octadecene and the like; unsaturated carboxylic acids such as 2-hexenoic acid and esters thereof, oleic acid and esters thereof including a triglyceryl esters having a relatively high oleic acid content, erucic acid and esters thereof including triglyceryl esters having a relatively high erucic acid content, ricinoleic acid and esters thereof including triglyceryl esters having a relatively high ricinoleic acid content, linoleic acid and esters thereof including triglyceryl esters having a relatively high oleic acid content; unsaturated alcohols such as 3-hexen-1-ol, 9-octadecen-1-ol and the like; unsaturated aldehydes such as 3-hexen-1-al, 9-octadecen-1-al and the like. In addition to the above, the organic substrate which can be used in the process according to the invention include alicyclic compounds having at least one internal carbon—carbon double bond and at least one terminal methyl group, a terminal carboxyl group and/or a terminal functional group which is oxidizable to a carboxyl group by biooxidation. Examples of such compounds include but are not limited to 3,6-dimethyl-1,4-cyclohexadiene; 3-methylcyclohexene; 3-methyl-1,4-cyclohexadiene and the like.

Examples of the aromatic compounds that can be used in the process according to the invention include but are not limited to arenes such as o-, m-, p-xylene; o-, m-, p-methyl benzoic acid; dimethyl pyridine, and the like. The organic substrate can also contain other functional groups that are biooxidizable to carboxyl groups such as an aldehyde or alcohol group. The organic substrate can also contain other functional groups that are not biooxidizable to carboxyl groups and do not interfere with the biooxidation such as halogens, ethers, and the like.

A cosubstrate may be provided to the culture during that stage of the fermentation when the culture is actively oxidizing the substrate to products. This is especially true if no net useable carbon or energy can be recovered from the substrate reaction itself, then this carbon and energy is provided by the cosubstrate.

The cosubstrate is a fermentable carbohydrate such as glucose, fructose, or maltose; or other fermentable organic compound, for example, glycerol, sodium acetate, methanol, or short chain alcohols; or mixtures thereof. The preferred cosubstrate is glucose, preferably a liquid glucose syrup, for example, 95% dextrose-equivalent syrup, or even lower dextrose-equivalent syrups. Such materials contain small amounts of disaccharides, trisaccharides, and polysaccharides which can be hydrolyzed during the fermentation by the addition of an amylase enzyme such as α-amylase, glucoamylase and cellulase. Thus glucose can be provided in situ in a reaction simultaneous with the biooxidation.

It is convenient, but not absolutely necessary, if the carbon and energy source used to grow the biomass is the same as the cosubstrate used to drive the oxidative conversion reaction. The practical benefit is that fewer raw materials need be handled and the various stages of the fermentation can be well integrated. Thus a single cosubstrate sterilization and delivery system can be used to deliver both the carbon and energy source to grow the biomass and the cosubstrate to drive the oxidation reaction.

The microorganism that can be used in the process according to the invention is any microorganism capable of biooxidizing the substrate as defined herein. The microorganism can be any microorganism in which beta oxidation is partially or completely blocked by disruption, inactivation or deletion of one or more acyl CoA oxidase gene(s); any yeast in which beta oxidation is partially or completely disrupted by inactivation or deletion of one or more acyl CoA oxidase gene(s); any *Candida* strain where beta oxidation is partially or completely disrupted by inactivation or deletion of one or more acyl CoA oxidase gene(s). When the fermentation process involves the biooxidation of a substrate to a carboxylic acid, the microorganism will normally be a yeast. Such a microorganism is capable of oxidizing the substrate in such a way that the mono- and/or dicarboxylic acids formed are not further oxidized by degradation leading to chain shortening. However, the process according to the invention pertains to the use of any microorganism.

Yeast strains known to excrete alpha, omega-dicarboxylic acids as a by-product when cultured on alkanes or fatty acids as the carbon source are set forth in U.S. Pat. No. 5,254,466, the entire contents of which are herein incorporated by reference. These strains are partially or completely oxidation-blocked strains; that is, they are genetically modified so that the chromosomal POX4A, POX4B and both POX5 genes have been disrupted. The substrate flow in this strain is redirected to the omega-oxidation pathway as the result of functional inactivation of the competing β-oxidation pathway by POX gene disruption. A completely oxidation-blocked strain is a *C. tropicalis* strain, strain H5343 (ATCC 20962), which is described in U.S. Pat. No. 5,254,466.

Another suitable strain is one in which one or more reductase genes are amplified resulting in an increase in the amount of rate-limiting omega-hydroxylase through P450 gene amplification and an increase in the rate of substrate flow through the ω-oxidation pathway. Strains which selectively increase the amount of enzymes known to be important to the oxidation of fatty acids are also preferred. Such strains contain increased copies of the CYP and CPR genes. These genes have been identified as those relating to the production of the ω-hydroxylase complex catalyzing the first step in the oxidation pathway. Strain HDC1 is an example of a strain that contains multiple copies of the CYP 52A2A gene integrated into the genome of strain H5343. This strain and similar strains are described in copending application Ser. No. 60/083,798, filed on May 01, 1998, the entire contents of which are incorporated herein by reference. Other strains that can be used with the methods of this invention are *C. tropicalis* strains HDC1, HDC5, HDC10, HDC15, HDC20, HDC23, HDC 23-1, HDC 23-2, and HDC 23-3 as are described in PCT/US99/20797, the entire content of which is hereby incorporated by reference.

Suitable sources of inorganic nitrogen include any ammonium-containing compounds. Examples thereof include, but are not limited to, alkali metal nitrates or ammonium salts such as ammonium sulfate, ammonium chloride, ammonium nitrate and ammonium acetate. Preferred nitrogen sources are ammonium salts or compounds that generate ammonia through the metabolic action of the organism like urea. A particularly preferred source of inorganic nitrogen for use in the present invention is ammonia.

The fermentation process can be modified by utilizing a triglyceride fat or oil as the source of both the organic substrate and cosubstrate. A lipase, formulated with the fermentation broth, hydrolyzes or splits the fat or oil into fatty acids and glycerine. Glycerine consumption by the organism serves to drive the splitting reaction to completion while supplying the energy necessary to convert the free fatty acids to their corresponding dibasic acids. Lipases that are oleo-specific are particularly preferred. Oleo-specific lipases exhibit a high selectivity for a triglyceride having a high oleic acid content and selectively catalyze the hydrolysis of the oleate ester groups. Examples of such oleo-specific lipases include but are not limited to the lipases produced by *Pseudomonas sp, Humicola lanuginosa, Candida rugosa, Geotrichum candidum,* and *Pseudomonas* (Burkholderia). A particularly preferred lipase is UNLipase from *Geotrichum candidum* ATCC No. 74170 described in U.S. Pat. No. 5,470,741, the entire contents of which are incorporated herein by reference.

The fermentation step is preferably carried out in three stages, growth phase, induction phase, and conversion phase. Each phase may be operated at the same or different fermentor conditions of temperature, pH, aeration, etc. Growth phase begins when the cell culture is introduced into the fermentor and a rapid phase of growth ensues. Growth may be exponential or sub-exponential depending on the composition of the medium employed. This continues until the culture reaches linear growth as measured by a decrease in oxygen consumption. Linear growth occurs when growth is limited by the rate of addition of a key nutrient to the medium; thus growth becomes proportional to the rate at which the limiting nutrient is supplied. Usually, in the process of this invention, the key nutrient will be the cosubstrate. The second phase is the induction phase. In the induction phase key metabolic activities are initiated that begin the desired conversion of substrate to product. The culture can be maintained in a linear growth phase for a period of time before inducing the culture. The inducing agent will usually be the substrate itself, but for compounds that do not initiate their own conversion, another inducing agent may be used in concert with the substrate. The induction phase can be used to transition the rapid growth phase to the conversion phase. The fermentation moves into the next phase, conversion phase, when the substrate is converted to product.

During the conversion phase, the fermentation broth is in an acidic pH range of between 2 and 7. The preferred operating pH range is from about 3.5 to 7.0, even more preferred range is from about 5.0 to about 6.5. pH may be controlled by automatic titration using a strong base, examples of which are, sodium hydroxide solution, potassium hydroxide solution, ammonium hydroxide solution, or ammonia gas. Note that by operating the fermentation in this pH regime compared to prior art methods that ammonia can be used for pH control since it will react to form the non volatile aqueous ammonium ion. Prior art methods for making dicarboxylic acid when operated in the alkaline pH regime would not effectively make the aqueous ammonium ion thus causing undesirable emissions of ammonia vapor in the offgas and toxic ammonia accumulation in the broth. The fermentation can be carried out at a temperature of from about 26° C. to about 40° C.

In the first stage, a culture medium is inoculated with an active culture of beta-oxidation blocked microorganism such as a beta-oxidation blocked C. tropicalis strain where a period of rapid exponential growth occurs. The pH of the culture medium is controlled by the addition of base, examples include but are not limited to ammonium hydroxide, potassium hydroxide, sodium hydroxide or ammonia gas. The cosubstrate addition to the fermentor is preferably a fed-batch addition during the conversion phase. The end of exponential growth phase is marked by a depletion of glucose, a rapid increase in dissolved oxygen, and, most sensitively, by a rapid increase in offgas oxygen and decrease in offgas $CO_2$. In the absence of an inducing substrate, biomass will continue to accumulate at a rate proportional to the glucose feed rate (i.e., linear growth). It is desirable to initiate the conversion phase either at the end of exponential growth or at a point when the desired biomass level has been attained. If the oxygen transfer characteristics of the production vessel are such that the desired biomass level can not be reached by maintaining the culture in exponential growth, then a combination of exponential growth followed by a linear glucose-limited growth phase (induction phase) can be used to achieve a given biomass level.

To maintain the culture in a healthy state during the transition to glucose limited linear growth, it may be desirable to start a glucose feed during growth so that glucose will always be available to the culture. The glucose level in the initial medium charge is selected based on the total glucose desired for growing the microorganism less the amount that will be fed during growth. The glucose feed may be started at any time from the beginning of growth. However because there is some variation in inoculum quality and lag phase after inoculating the production vessel, it is preferred to start the glucose feed during exponential growth phase at some predetermined biomass concentration, as judged by direct biomass measurements, or indirect methods like optical density, carbon dioxide evolution rate, or oxygen uptake rate. The glucose may be a corn syrup refined or unrefined. The glucose may be fed from the top of the vessel through the vapor space as a continuous stream or as a continuous series of pulses or impulses. The glucose feed may also be fed into the vessel under the surface especially into a region of high shear near the agitator to attain a rapid distribution throughout the vessel. In large vessels there may be multiple glucose feed points within the same vessel.

The conversion phase where the substrate is oxidized is initiated by adding an inducer and the substrate containing an oxidizable methyl group. In the case of alkanes, fatty acids, fatty acid methyl esters and fatty acid salts; these substances and combinations thereof induce their own oxidation to dicarboxylic acids and may be useful for inducing the oxidation of other substances. The substrate may be added batchwise or as a continuous feed or as a series of continuous pulses or impulses. The substrate may be added from the top of the vessel through the vapor space or under the surface especially into a region of high shear. In large vessels there may be multiple substrate feed points. The oxidation is conducted at an acidic pH less than 7 and preferable near or below the pKa of the carboxyl group being formed by the oxidation or is present in the substrate.

It is preferable to progressively decrease the glucose feed rate to the fermentor as the conversion proceeds to prevent the accumulation of biomass and triacylglycerol esters. With the conversion of commercial oleic acid, the accumulation of intracellular storage vacuoles is a useful indicator of the glucose feed rate needing adjustment. Adjustments are done by decreasing the feed rate by about 5% to 25% and usually about 10% per each 24 hours of the conversion phase. Other indicators could also be used such as base utilization rate, $CO2$ evolution rate, or respiratory quotient.

One problem often encountered in the fermentation process is the formation of carboxylic acid soaps and foaming as a result of working in the traditional alkaline pH range. In an alkaline environment, carboxylic acids form soaps which lead to unwanted foaming of the fermentation broth. The result of the soap formation is a decrease in the pH of the broth which is adjusted by adding a base such as caustic to the broth to maintain the pH of the broth at the desired value. Also, addition of glucose to the basic environment results in formation of carbonates that affect the pH of the fermentation broth. To compensate for the effects on the pH of soap and carbonate formation, large quantities of base must be added to maintain the pH of the broth at the desired level.

It has surprisingly been found that by carrying out the fermentation process in an acidic pH range of from 2 to 7, preferably from 3 to 7 and even more preferably from 5 to 6.5, rather than a caustic pH range, foaming is substantially reduced and the formation of carbonate from carbon dioxide produced during the metabolism of glucose is reduced thereby substantially reducing the amount of raw material needed to control the pH of the fermentation broth. By carrying out the fermentation process at an acidic pH, these problems are substantially reduced resulting in decreased amounts of base used during the fermentation process. There is a net consumption of cation equivalents over anion equivalents during the growth reaction that contributes to a depression of culture medium pH. It is desirable to control the medium pH within the range from 2–7, and preferably from about 3–6.5 during growth by the addition of base on pH control. Among the bases useful for this purpose are ammonium hydroxide, ammonia, sodium hydroxide, and potassium hydroxide. It is desirable to select a base composition that provides one or more of the major nutrients consumed during growth such as ammonium hydroxide, ammonia, or potassium hydroxide. The growth medium formulation is adjusted to take into account the addition of the pH control reagent. Using $NH_4OH$ or ammonia gas to control the pH reduces the number of raw materials needed to grow the microorganisms by combining the pH control agent and the nitrogen source into one raw material added to the fermentor.

With respect to using nitrogen sources such as ammonia or ammonium hydroxide it is necessary to have only 250 ppm or less nitrogen source present in the medium to initiate growth and the consumption of these pH control reagents. The ammonia concentration will therefore remain nearly constant during growth of the culture. Thus the desired concentration of ammonia in the medium at the time of induction can be conveniently preselected by adding ammonia or ammonium salts to the initial medium charge. Useful sources of ammoniacal nitrogen for the initial fermentor charge include ammonia phosphate, ammonium sulfate, ammonium nitrate, ammonia, urea, and ammonium hydroxide.

Another aspect of the invention relates to a formulation of a fermentation medium useful for propagating *Candida tropicalis* and gives a high productivity for converting substrates having oxidizable methyl groups to carboxylic acids. By adjusting feed rates of materials into the fermentation broth, the growth of the microorganism can be controlled. The major nutrients consumed during growth of the microorganism on glucose are ammoniacal nitrogen, potassium, magnesium, phosphate, and sulfate. Sodium and calcium are not consumed, however calcium should be present at a concentration of about 5–50 ppm or more to obtain normal growth depending on the formulation of the inoculum medium. Trace minerals and biotin are also included in the medium. The biotin may be a relatively pure grade or supplied as a more crude grade such as in biotin yeast, yeast extracts, or corn steep liquor.

Useful sources of phosphate are ammonium phosphate, potassium phosphate mono, di, and tribasic, sodium phosphate, mono, di, and tribasic, and phosphoric acid. Useful sources of potassium are potassium sulfate, potassium phosphate, mono, di, and tribasic, and caustic potash.

A fermentation aid can be used in the oxidation of alkanes and/or the oxidation of fatty acids. The preferred fermentation aid is a fatty acid ester, a particularly preferred fermentation aid is a methyl ester. One major benefit of the use of such a fermentation control agent is in foam control and controlling the fluid characteristics of the fermentation broth. If product chain length distribution is important in ultimate product performance, it is desirable to select a chain length of the methyl ester that resembles the alkane or fatty acid since the methyl ester will also be converted to product. The ester may be added batch wise or blended into the feed. If blended into the feed, it may comprise about 10% or less and preferably about 1% or less of the feed. Some commercial fatty acids naturally contain some methyl esters and may be used directly as substrates for dicarboxylic acid production. For example, EMERSOL® 267 (Cognis Corporation) is a commercial oleic acid containing about 1% or less methyl esters and has been found to be a good substrate in this invention. A typical technical grade of oleic acid, EMERSOL® 267, that is used in the process has the approximate composition 0.3% C12, 2.4% C14, 0.6% C14:1, 4.7% C16, 4.6% C16:1, 0.2% C17, 0.8% C18, 69.9% C18:1, 10.5% C18:2, 0.3% C18:3.

In the case of alkane oxidations to dicarboxylic acids, it has further been found useful to use a fatty acid or fatty acid salt as a fermentation aid. This results in a better distribution of the alkane throughout the fermentation broth. The fatty acid may be added batchwise or may be formulated into the alkane feed. If formulated into the feed, fatty acid or fatty acid salt may typically comprise about 10% or less and preferably about 5% or less of the feed. Here too, if product chain length distribution is important in ultimate product performance, it is desirable to select a chain length distribution of the fatty acid that resembles the alkane since the fatty acid will also be converted to product.

It has surprisingly been found that particular combinations of fatty materials, for example fatty acids and fatty esters, cause fine aqueous suspensions of long chain dicarboxylic acids to form highly defined particles at temperatures below 50° C. Other fatty materials might also be used separately or in combination, including fatty alcohols, fatty ethers, etc. and are considered a part of this invention. The resulting suspensions have desirable shear-thinning characteristics that facilitate their handling and practical application. It is desirable that the particles so formed in the suspension have sizes within a narrow size distribution. This aspect of the invention is well suited for application in large-scale production equipment. Indeed, superior performance occurred in such equipment compared with laboratory scale equipment. This suggests that wall effects may play a role in particle growth.

Useful fatty materials include saturated and unsaturated fatty acids C10 –C20 and their esters that include, but are not limited to, sunflower fatty acids, sunflower fatty acid methyl esters, tallow fatty acids, and tallow fatty acid methyl esters. Examples of typical commercial compositions of these materials are shown in Table 1. Each composition listed below is commercially available from Cognis Corp., Cincinnati, Ohio.

TABLE 1

Compositions of Example Additives

| Additive Trade Names | High oleic sunflower fatty acids Emery® 244 Edenor® PK 1805 | Methyl Tallowate Emery® 2203 | High-oleic Sunflower fatty acid methyl esters Edenor® ME-V 05 | Methyl Oleate Emery® 2301 |
|---|---|---|---|---|
| Fatty Acid | Fatty Acid Distribution (%) | | | |
| C10   |       | 0.05  |       |       |
| C12   | 0.11  | 0.65  |       |       |
| C14   | 0.11  | 2.80  |       | 3.0   |
| C14:1 | —     | 0.47  |       | 2.0   |
| C15   | 0.15  | 0.45  | 0.29  |       |
| C15:1 |       | 0.21  | —     |       |
| C16   | 3.87  | 23.82 | 4.17  | 4.0   |
| C16:1 | 0.09  | 2.46  | 0.10  | 6.0   |
| C17   | —     | 1.26  | —     | 1.0   |
| C17:1 |       | 0.68  | —     |       |
| C18   | 4.73  | 19.00 | 4.48  |       |
| C18:1 | 84.45 | 42.20 | 87.4  | 76.0  |
| C18:2 | 5.24  | 2.54  | 2.91  | 7.0   |
| C18:3 | 0.43  | 0.25  | —     | 1.0   |
| C20:1 | 0.30  | 0.33  | —     |       |

The dicarboxylic acids prepared in fermentation broths typically exist as needle-like crystals from 1–10 $\mu$m in length. The composition of the diacids reflect the chain length of the substrate being oxidized. Such fermentation broth can be highly viscous to the point of being solid. When a fatty material as described herein is applied to such a fermentation, it is possible grow, in situ, substantially disk-shaped, substantially partially spherical (e.g., cup-shaped) and/or substantially spherical dicarboxylic acid particles about 15–40 $\mu$m or more in diameter and about 1–5 $\mu$m in thickness at temperatures below about 50° C. In one embodiment of the present invention, substantially spherical particles were generated having a diameter of approximately 1 cm. Thus, it is contemplated that dicarboxylic acid particles produced in accordance with the present invention may range from about 1 $\mu$m to about 1 cm or more in diameter and/or thickness. When fatty materials described herein are applied to fermentations generating or containing dicarboxylic acids, the resulting broth has a low apparent viscosity allowing fermentation broth handling to continue under optimal conditions. For convenience, the term "disk shaped" may be used herein to also refer to substantially partially spherical particles. "Substantially" is used herein to mean both approximately and precisely.

In the case of fermentation reaction generating dicarboxylic acids, a desirable benefit of using such fatty materials is that these reagent additives can also potentially be converted to dicarboxylic acids. This simplifies the recovery of the dicarboxylic acids from the broth so that additional processing to remove the additive is not needed.

Certain commercially available fatty acid preparations can be used directly to cause formation of disk shaped particles because, in their manufacturing process, fatty derivatives are left behind that cause the desired particle growth and size distribution in the fermentation. Examples of these include Emersol® 267 Oleic acid (commercially available from Cognis Corp., Cincinnati, Ohio), which contains low levels of methyl ester, and partially-hydrolyzed fatty acids, which contains low levels mono-, di-, and tri-glycerides. In the case of a dicarboxylic acid fermentation, one can therefore make a judicious selection of substrate from commercially available substrates having been informed of the methods of this invention.

It is contemplated that fatty materials may be used in the various fermentation media described herein along with a variety of antifoams such as those of the silicone and polypropylene glycol types without inhibitory effect on particle growth.

The fatty material may be added to the aqueous suspension of dicarboxylic acids batchwise or fed-batch. In general the levels of fatty materials used may range from about 10 ppm to about 5% or more, but preferably about 50 ppm to about 1%, based on the mass of dicarboxylic acid. Particle growth occurs so long as a minimal level of additives is present. It is believed that the fatty acid additives aid the dicarboxylic acid particle growth while fatty acid esters and other fatty derivatives aid in providing a narrow distribution of particle sizes.

In the case of a fermentation generating dicarboxylic acids from hydrocarbons it is desirable to add a combination of fatty derivatives including fatty acids and fatty acid methyl esters. It is most convenient to blend these materials into the hydrocarbon feed in order to simplify the preparation, sterilization, and feeding of the additives to the fermentation.

Likewise, in the case of a fermentation generating dicarboxylic acids from a fatty acid, it is desirable to add a similar corresponding methyl ester. Thus the additive will not alter the chain length distribution of the dicarboxylic acid product.

Many combinations and applications are possible in practicing this invention having disclosed these methods for growing dicarboxylic acid disk particles and describing the benefits on rheological properties of the suspension.

It has surprisingly been found that by maintaining dissolved oxygen concentration levels below about 25% and preferably below 20%, relative to saturation with air, that there is a reduction in the amount of cosubstrate needed during the conversion phase. When the concentration of dissolved oxygen is below these levels, glucose is more efficiently utilized in providing energy for oxidation. Consequences of adding too much glucose include the further accumulation of biomass and triacylglycerol esters with diminished carboxylic acid production during the conversion phase.

Triacylglycerol ester formation, in oleaginous yeasts, can be controlled or minimized in part by adjustment of the magnesium concentration or ratio of magnesium to phosphate in the initial medium charge. The preferred magnesium concentration is about 0.1 to about 1.0 gm/L and more preferably about 0.2 to about 0.8 g/L concentration in the fermentation inoculum. The preferred phosphate: magnesium ratio is 20:1 to about 2:1, preferably 15:1 to about 3:1.

It has also surprisingly been found that the fermentation broth during the conversion phase accumulates a heat-labile catalase-like activity that consumes $H_2O_2$. This may interfere with glucose concentration assays that measure $H_2O_2$ produced from glucose oxidase.

A preferred embodiment of the process according to the invention is the preparation of 9-octadecenedioic acid by biooxidation of oleic acid. While any grade of oleic acid can be used as the substrate, a typical technical grade oleic acid consists of the following carboxylic acids: 0.42% $C_{12}$; 2.7% $C_{14}$; 0.86% $C_{14:1}$; 6.3% $C_{16}$; 4.6% $C_{16:1}$; 0.93% $C_{17}$; 2.8 $C_{18}$; 71.8% $C_{18:1}$; 8.3% $C_{18:2}$; 0.58% $C_{18:3}$. The oleic acid can also be a high oleic acid grade obtained from a fatty oil of a *Helianthus annuus* (sunflower seed oil) species described, for example, in U.S. Pat. No. 4,627,192, the entire contents of which are incorporated herein by reference. Other high oleic acid varieties of oilseeds may also be used in this process. Such oils are very rich in oleic acid and contain at least 70–80% by weight of oleic acid.

The present invention will be better understood from the examples which follow, all of which are intended for illustrative purposes only, and are not meant to unduly limit the scope of the invention in any way. In all the examples, component concentrations are shown in their anhydrous forms. Commercially available hydrates of the listed components may be used if the concentration is appropriately adjusted to include waters of hydration.

EXAMPLE 1

Fermentation media in accordance with the present invention were prepared, the components of which are listed in Tables 2 and 3, below.

TABLE 2

| Synthetic Production Medium Components | Concentration (g/L) |
| --- | --- |
| Glucose | 27.0 |
| Ammonium Sulfate | 7.0 |
| Potassium Phosphate, Monobasic | 5.1 |
| Magnesium Sulfate | 0.5 |
| Calcium Chloride | 0.1 |
| Citric Acid | 0.06 |
| Ferric Chloride | 0.023 |
| Biotin | 0.0002 |
| Trace Metals: | |
| Boric Acid | 0.0009 |
| Cupric Sulfate | 0.00007 |
| Potassium Iodide | 0.00018 |
| Ferric Chloride | 0.00036 |
| Manganese Sulfate | 0.00072 |
| Sodium Molybdate | 0.00036 |
| Zinc Sulfate | 0.00072 |
| Water | Balance |
| SAG 471 ® Antifoam | 0.8 ml |

The medium components of Table 2 were heat sterilized in a suitable manner to avoid any precipitation reactions, then combined in a sterile fermentor vessel upon cooling. The complete, uninoculated medium was found to be completely clear with a slight straw color and no strong odors. Addition of the antifoam yielded slight turbidity. *Candida tropicalis* H5343 ALK 2-1 was grown under sterile conditions on the medium listed in Table 2 in a stirred, aerated fermentor with an initial liquid volume of 12 L. The sterile culture medium was inoculated with a 5% inoculum of *Candida tropicalis* H5343 ALK 2-1 and grown at 35° C., pH 5.8 for approximately 10 hours with agitation and aeration rates sufficient to keep the dissolved oxygen above 20%. When the culture stopped growing exponentially and the dissolved oxygen began to rise, the conversion phase was commenced by starting a continuous feed stream of Exxon Developmental Fluid 137 (a hydrocarbon containing approximately 94.4% Tridecane, the balance being primarily dodecane) mixed with the fermentation aids 1.25% Emersol ®267 (a technical grade of oleic acid) and 1.25% Emery® 2203 (a technical grade of methyl tallowate) at a rate of 0.7 g/L/hr. Simultaneously, the temperature in the fermentor was reduced from 35° C. to 30° C., the aeration rate was reduced to 0.4 vvm, and 0.4 bar of backpressure was applied to the vessel. The pH was maintained between 5.8–5.9 during the growth and conversion phase with 6N KOH. A continuous glucose feed stream was started to the fermentor at a rate of 1.58 g/L/hr glucose when the biomass concentration reached approximately 10 g/L. The glucose feed rate during conversion was reduced between 0–15% on a daily basis based upon the microscopic observation and assessment of accumulating storage vacuoles within the yeast cell. 7 ml of PPG (polypropylene glycol) antifoam was added to the fermentor during conversion to control mild foaming. After 50 hours of the conversion phase, the whole broth in the fermentor contained 41.5 g/Kg 1,13-tridecanedioic acid.

EXAMPLE 2

TABLE 3

| Synthetic Production Medium Components | Concentration (g/L) |
| --- | --- |
| Glucose | 27.0 |
| Potassium Phosphate, Monobasic | 4.9 |
| Magnesium Sulfate | 0.6 |
| Calcium Chloride | 0.1 |
| Citric Acid | 0.06 |
| Ferric Chloride | 0.023 |
| Biotin | 0.000012 |
| Trace Metals: | |
| Cupric Sulfate | 0.00007 |
| Manganese Sulfate | 0.00432 |
| Zinc Sulfate | 0.00072 |
| Citrate | 0.00708 |
| Water | Balance |
| SAG 471 ® Antifoam | 0.6 ml |

The medium components of Table 3 were sterilized in a suitable manner to avoid any precipitation reactions and combined in a sterile fermentor vessel. The complete, uninoculated medium was found to be completely clear with a slight straw color and no strong odors. *Candida tropicalis* H5343 HDC 23-3 was grown under sterile conditions on the medium listed in Table 3 in a stirred, aerated fermentor with an initial liquid volume of 12 L. The sterile culture medium was inoculated with a 3% inoculum of *Candida tropicalis* H5343 HDC 23-3 and grown at 35° C. for approximately 12 hours with agitation and aeration rates sufficient to keep the dissolved oxygen above 20%. The pH was adjusted to and maintained between 5.8–5.9 during the growth phase with the addition of 6N $NH_4OH$ which was also the source of inorganic nitrogen in the medium. When the culture stopped growing exponentially and the dissolved oxygen began to rise, the conversion phase was commenced by adding an inducing charge and simultaneously starting a continuous feed stream of High Oleic Sunflower Fatty Acids (containing 84.4% oleic acid, 5.2% linoleic acid, 4.7% stearic acid, 3.9% palmitic acid, with the balance comprising small amounts of eicosanoic acid (20:0), eicosaenoic acid (20:1), pentadecanoic acid, lauric acid, and myristic acid) at a rate of 2.0 g/L/hr. Simultaneously, the temperature in the fermentor was reduced from 35° C. to 30° C., the aeration rate was reduced to 0.4 vvm, and the pH control reagent was switched from $NH_4OH$ to NaOH. The pH was maintained between 5.8–5.9 during the conversion phase with 6N NaOH. A continuous glucose feed stream was started to the fermentor at a rate of 1.22 g/Uhr glucose when the biomass concentration reached approximately 10 g/L. The glucose feed rate during conversion was reduced between 0–45% on a daily basis based upon the microscopic observation and assessment of accumulating storage vacuoles within the yeast cell. No additional antifoam was used during the conversion phase. After 50 hours of the conversion phase, the whole broth in the fermentor contained 71 g/Kg total dicarboxylic acids.

EXAMPLE 3

TABLE 4

| Synthetic medium formulation Medium Components | Concentration (g/L) |
| --- | --- |
| Glucose | 20.0 |
| Ammonium Sulfate | 0.5 |
| Potassium Phosphate, Monobasic | 5.1 |
| Magnesium Sulfate | 0.9 |
| NaCl | 0.5 |
| Calcium Chloride | 0.1 |
| Biotin | 0.0002 |
| Trace Metals: | |
| Boric Acid | 0.00075 |
| Cupric Sulfate | 0.00006 |
| Potassium Iodide | 0.00015 |
| Ferric sulfate | 0.04 |
| Ferric Chloride | 0.0003 |
| Manganese Sulfate | 0.0006 |
| Sodium Molybdate | 0.0003 |
| Zinc Sulfate | 0.0006 |
| Water | Balance |
| SAG 471 ® Antifoam | 2 drops |

The medium components of Table 4 were sterilized in a suitable manner to avoid any precipitation reactions, then combined in a sterile fermentor vessel. The medium was found to be completely clear with a slight color and little odor. Addition of the antifoam yielded slight turbidity. The pH of the medium was initially adjusted to pH 5.8 using 6N ammonium hydroxide solution. *Candida tropicalis* H5343 (ATCC 20962) was grown on this medium in a stirred and aerated fermentor using a 4% inoculum prepared in a medium having similar composition. Exponential growth began following a brief lag phase. A glucose feed was started at a rate of 1.25 g/L/hr based on the initial medium volume when the culture contained about 5 g/L biomass dry weight as judged by optical density measurements. Exponential growth continued for about nine hours when the glucose became growth limiting with only a slight decrease in exponential growth rate over the period.

At the end of this period of rapid growth, the pH control reagent was changed to 6N potassium hydroxide solution and the glucose feed was kept constant for the next 110 hours. During this period, ammonium, which concentration remained constant throughout exponential growth, was depleted from the medium and phosphate concentration dropped to low levels. Biomass continued to accumulate in the medium at a constant linear rate despite the consumption of these key nutrients. Viable cell counts also increased linearly until the ammonium was depleted from the medium, after which they remained constant. Ultimately, the fermentation produced 71.5 g/L biomass dry weight.

COMPARATIVE EXAMPLE 1

| Production Medium Components | Concentration (g/L) |
| --- | --- |
| Glucose | 40.0 |
| Ammonium Sulfate | 8.0 |
| Corn Steep Liquor | 9.0 |
| Potassium Phosphate, Monobasic | 2.0 |
| Potassium Phosphate, Dibasic | 1.0 |
| Magnesium Sulfate | 0.5 |
| NaCl | 0.5 |
| Calcium Chloride | 0.1 |
| Trace Metals: | |
| Boric Acid | 0.00075 |
| Cupric Sulfate | 0.00006 |
| Potassium Iodide | 0.00015 |
| Ferric Chloride | 0.0003 |
| Manganese Sulfate | 0.0006 |
| Sodium Molybdate | 0.0003 |
| Zinc Sulfate | 0.0006 |
| SAG 471 ® Antifoam | 2 drops |

The medium components of Comparative Example 1 were sterilized in a suitable manner to avoid any precipitation reactions and combined in a sterile fermentor vessel. The complete, uninoculated medium was found to be very dark with a strong odor characteristic of corn steep liquor. *Candida tropicalis* H5343 (ATCC 20962) was grown under sterile conditions on the medium listed in Table 4 in a stirred, aerated fermentor with an initial liquid volume of 10 L. The sterile culture medium was inoculated with a 6% inoculum of *Candida tropicalis* H5343 (ATCC 20962) and grown at 35° C. for approximately 9.5 hours with agitation and aeration rates sufficient to keep the dissolved oxygen above 20%. 5 ml of SAG 471 antifoam was added to the fermentor during growth to control foaming in the culture. The pH was maintained between 5.8–5.9 during the growth phase with the addition of 6N $NH_4OH$. When the culture stopped growing exponentially and the dissolved oxygen began to rise, the conversion phase was commenced by starting a continuous feed stream of Emersol®R267 (a commercial grade of Oleic acid containing containing 71.8% oleic acid, 8.3% linoleic acid, 6.3% palmitic acid, 4.6% palmitoleic acid, 2.8% stearic acid, 2.7% myristic acid, 0.93% C17:0 acid, 0.86% myristoleic acid, 0.58% linolenic acid, and 0.42% lauric acid) at a rate of 2.0 g/L/hr. Simultaneously, the temperature in the fermentor was reduced from 35° C. to 30° C., the aeration rate was reduced to 1.2 vvm, and the pH control reagent was switched from $NH_4OH$ to KOH. The pH was maintained at or above 5.8 during the conversion phase with 6N KOH. A continuous glucose feed stream was started to the fermentor at a rate of 1.8 g/L/hr glucose at the end of the exponential growth immediately preceding the start of the conversion phase. This same glucose feed rate was maintained to the fermentor throughout the conversion phase. 17 ml of SAG 471 antifoam was added to the fermentor during the first 3 hours of the conversion phase to control very heavy foaming. After 50 hours of the conversion phase, the whole broth in the fermentor contained 64 g/Kg total dicarboxylic acids.

EXAMPLE 4

Modification of an Aqueous Suspension of Dodecanedioic acid

A 25 g/l finely-divided aqueous suspension of long-chain dicarboxylic acid was prepared by first, dissolving 12.5 grams of dodecanedioic acid, 99%, a Dupont product (Aldrich Chemical Company) (DDDA), into water using excess KOH to form the water-soluble dicarboxylate. The solution was then rapidly titrated to pH 6 using $H_2SO4$ to precipitate the diacid.

Twenty milliliters of this suspension was distributed to each of eight flat bottom screw cap vials equipped with a stirring bar. Thus each vial contained 0.5 grams of finely divided dodecanedioic acid suspended in water. These were placed in a water bath at 30° C. on a magnetic stirrer and the suspension allowed to equilibrate with stirring overnight.

The effect of various additives on the suspension behavior was tested by batch adding the test substances at various concentrations in the equilibrated vials. The compositions of the commercial test substances are shown in Table 1. The net formulations in each of the vials are shown in Table 5.

TABLE 5

Additive Effects Testing for Aqueous Dicarboxylic Acid Suspensions

| Vial | Additive | Amount (µg) | Ratio of Additive/DDDA (ppm) |
| --- | --- | --- | --- |
| 1 | Oleic Acid | 44 | 88 |
| 2 | Oleic Acid | 88 | 176 |
| 3 | Methyl tallowate | 44 | 88 |
| 4 | Methyl tallowate | 88 | 176 |
| 5 | Methyl oleate | 44 | 88 |
| 6 | Methyl oleate | 88 | 176 |
| 7 | None (control) | 0 | 0 |

Test Volume = 20 ml
Test Temperature = 30° C.
Dodecanedioic acid in suspension = 0.5 grams The appearance and behavior of the suspensions were observed 4 hours, 24 hours, or longer after adding the test additives and compared with the control (Vial 7). The control appeared as a suspension with some association of individual particles as viewed under a phase contrast microscope.

Both methyl ester additives at both concentrations gave better association of the DDDA into discrete particles of similar size (Vials 3–6). This was apparent when the vials were removed from stirring and allowed to settle. The suspensions with the methyl ester additives settled much more rapidly than the control. The remaining aqueous phase was clear compared to the control, which remained turbid with the smaller DDDA particles remaining in suspension.

The most surprising results were obtained in suspensions with the oleic acid additives where in 4 hours, the particles began to associate into large masses. At twenty hours, Vial 1 had large dense masses of DDDA near the bottom and some smaller masses at the top of the vial. At twenty hours, Vial 2 contained a single sphere of DDDA about 1 cm in diameter and the aqueous phase was clear.

As vials 1 and 2 continued to be incubated beyond 20 hours, pieces of the larger masses had become broken. These pieces then attached to the stirring bar itself. Ultimately all the DDDA grew onto the stirring bar such that the vial contained a whirling chunk of DDDA in clear water.

This example demonstrates how the addition of fatty acids and fatty acid derivatives may be used to make aqueous suspensions of dicarboxylic acids more amenable to separations by processes using filtration, sedimentation, or size classification.

EXAMPLE 5

Viscosity of Aqueous Dicarboxylic Acid Suspensions: Effect of Particle Morphology An approximately twelve-percent (117.0 g/kg) aqueous suspension of saturated and unsaturated dicarboxylic acids primarily C16-C18 was prepared in a fermentation broth from high oleic acid sunflower oil using a microorganism at 30° C. During the fermentation, methyl oleate was added fed-batch to the fermentation broth at a rate to provide about a 1% ratio of methyl oleate to dicarboxylic acids. A sample of broth was collected for phase contrast microscopic observation and viscosity measurements as shown in Table 6.

For comparison, the sample was then heated to 70° C. and rapidly cooled to room temperature to disrupt the disk structures that had formed in the original broth. This was then subjected to similar analysis as is also shown in Table 6.

TABLE 6

Effect of Particle Morphology on Brookfield Viscosity of an approximately 12% Aqueous Fermentation Broth Suspension of Dicarboxylic Acids.

| Sample | Particle Appearance | Spindle Number/ Spindle Speed (rpm) | Viscosity (cP) @ 21° C. |
|---|---|---|---|
| Fermentation broth | cup-shaped disks 25–30 µm diameter, 5 µm thick | Spindle 2/ 3 rpm | 5,000 |
| Fermentation Broth Heated then cooled | needle-like crystals | Spindle 4/ 0.3 rpm | 1,000,000 |

A series of similar experiments were conducted at different concentration levels of dicarboxylic acid in suspension which confirmed the above results since they behaved in substantially similar fashion. Such concentrations were as follows: 27.6 g/kg, 57.3 g/kg, 83.2 g/kg, 95.8 g/kg, 100.9 g/kg, 117.0 g/kg, and 117.0 g/kg for a heat killed sample.

These results demonstrate the striking effect fatty acid derivatives have on dicarboxylic acid morphology and viscosity in a fermentation broth.

EXAMPLE 6

Effects of Various Fatty Acid Derivatives and Concentrations on Diacid Precipitate Morphology Various levels and types of fatty acid derivatives were tested in similar fermentations as in Example 5 and samples examined microscopically to determine the effect on dicarboxylic acid particle growth. Table 7 shows several combinations of substrates used for dicarboxylic acid production, combinations of additive fatty acid derivatives, and resulting appearance under a phase contrast microscope of dicarboxylic acids in suspension.

TABLE 7

Effect of Fatty Acid Derivative Additives on Suspension Morphology in a Fermentation Broth

| Substrate being Oxidized to Dicarboxylic Acids | Suspension Modifiers Added (ratio to diacids) | Appearance of Suspended Dicarboxylic Particles |
|---|---|---|
| High-Oleic Sunflower Fatty Acids | 1.0% Methyl oleate | Disk to cup-shaped, narrow distribution around 30 µm diameter by 5 µm thick |
| High-Oleic Sunflower Fatty Acids | 0.1% Methyl oleate | Single narrow distribution disk-shaped around 15 µm diameter |
| Partially hydrolyzed High-Oleic Sunflower Oil[1] | Contained 5% fatty acid glycerol esters | Single narrow distribution disk-shaped around 15 µm diameter |
| High-Oleic Sunflower Fatty Acids | None (comparative control for in situ fatty acid oxidations) | Bimodal distribution of disk sizes centering around 5 and 10 µm |
| Hydrocarbons Mixture[2] | 2.5% Emersol ® 267 + 2.5% methyl tallowate | Disk-skaped particles 20 µm in diameter |
| Hydrocarbons Mixture[2] | 1.25% Methyl oleate + 1.25% Oleic Acid | Single narrow distribution disk-shaped around 15 µm diameter |
| Hydrocarbons Mixture[2] | None (comparative control for in situ hydrocarbon oxidations) | Few disk shaped particles, most particles < 2 µm |

[1]high-pressure steam hydrolyzed oil having and Acid Value = 188.3 and Saponification Value = 198.5 indicating 95% hydrolysis of fatty acid triglycerol esters leaving a mixture of mono-, di-, and tri-glycerides to serve as precipitate modifiers.
[2]NORPAR ® 13 SOLVENT a product of Exxon Corporation containing normal aliphatic hydrocarbons C11 < 1%, C12 = 13%, C13 = 50%, C14 = 35%, C15 < 1%.

EXAMPLE 7

Viscosity of Aqueous Dicarboxylic Acid Suspensions: Shear-Thinning Characteristics The shear thinning characteristics of a 70.3 g/kg (~7%) aqueous suspension of C11–C15 saturated dicarboxylic acid was prepared in a fermentation broth using 1.25% each methyl oleate and oleic acid. Phase contrast microscopic examination of the broth showed the diacid suspension to contain disk-shaped dicarboxylic acid particles 15 μm in diameter. FIG. 1 shows the shear thinning characteristics of this aqueous suspension. A series of similar experiments were conducted at different concentration levels of dicarboxylic acid in suspension which confirmed the above results since they behaved in substantially similar fashion. Such concentrations were 17.8 g/kg, 26.4 g/kg and 59.9 g/kg.

What is claimed is:

1. A fermentation method which comprises conducting the fermentation in a fermentation medium and modifying the rheological properties of the fermentation medium containing a dicarboxylic acid by adding an effective dicarboxylic acid particle shape forming amount of a fatty material to the fermentation medium to cause formation of shaped dicarboxylic acid particles, wherein the shape is selected from the group consisting of substantially disk shaped, substantially partially spherical shaped and substantially spherical shaped.

2. A method for modifying the rheological properties of a fermentation medium containing a dicarboxylic acid according to claim 1 wherein the particles have a diameter greater than about 15 μm.

3. A method for modifying the rheological properties of a fermentation medium containing a dicarboxylic acid according to claim 2 wherein the diameter of the dicarboxylic acid particles ranges from about 15 μm to about 1 cm.

4. A method for modifying the rheological properties of a fermentation medium containing a dicarboxylic acid according to claim 1 wherein the thickness of the substantially disk-shaped or substantially partially spherical shaped dicarboxylic acid particles ranges from about 1 μm to about 15 μm.

5. A method for modifying the rheological properties of a fermentation medium containing a dicarboxylic acid according to claim 1 further comprising maintaining the temperature of the fermentation medium below about 50° C.

6. A method for modifying the rheological properties of a fermentation medium containing a dicarboxylic acid according to claim 1 wherein the fatty material is a fatty acid.

7. A method for modifying the rheological properties of a fermentation medium containing a dicarboxylic acid according to claim 1 wherein the fatty material is a fatty acid ester.

8. A method for modifying the rheological properties of a fermentation medium containing a dicarboxylic acid according to claim 7 wherein the fatty acid ester is a methyl ester.

9. A method for modifying the rheological properties of a fermentation medium containing a dicarboxylic acid according to claim 1 wherein the fatty material is added in an amount which provides greater than about 10 ppm based on the mass of the dicarboxylic acid.

10. A method for modifying the rheological properties of a fermentation medium containing a dicarboxylic acid according to claim 9 wherein the amount ranges from about 10 ppm to about 5% based on the mass of the dicarboxylic acid.

11. A method for modifying the rheological properties of a fermentation medium containing a dicarboxylic acid according to claim 10 wherein the amount ranges from about 50 ppm to about 1% based on the mass of dicarboxylic acid.

12. A method for modifying the rheological properties of a fermentation medium containing a dicarboxylic acid according to claim 1 wherein the fatty material is a combination of fatty acid and fatty acid ester.

13. A method for modifying the rheological properties of a fermentation medium containing a dicarboxylic acid according to claim 12 wherein the fatty acid ester is a methyl ester.

14. A method for modifying the rheological properties of a fermentation medium containing a dicarboxylic acid according to claim 1 wherein the fermentation medium includes (a) a source of metabolizable carbon and energy;

(b) a source of inorganic nitrogen;

(c) a source of phosphate;

(d) at least one metal selected from the group consisting of an alkali metal, an alkaline earth metal, transition metals, and mixtures thereof; and (e) a source of biotin, substantially free of particulate matter and bacteria.

* * * * *